United States Patent [19]

Barden

[11] 4,279,618
[45] Jul. 21, 1981

[54] METHOD AND APPARATUS FOR ANALYSIS OF TOTAL ATMOSPHERIC SULFURIC ACID CONTENT

[75] Inventor: James D. Barden, Chester, Md.
[73] Assignee: Versar, Inc., Springfield, Va.
[21] Appl. No.: 155,986
[22] Filed: Jun. 3, 1980
[51] Int. Cl.³ .................... G01N 25/68; G01N 21/72
[52] U.S. Cl. .................... 23/232 R; 23/232 E; 422/88; 422/91
[58] Field of Search ............ 23/232 R, 232 E; 422/88, 91, 54; 73/23

[56] References Cited

U.S. PATENT DOCUMENTS

| | | | |
|---|---|---|---|
| 3,550,429 | 12/1970 | MacMurtrie et al. | 73/23.1 |
| 3,692,481 | 9/1972 | Mitchell | 23/232 E |
| 3,948,602 | 4/1976 | Solomon | 23/232 E |

OTHER PUBLICATIONS

Scaringelli et al., "Determination of Atmospheric Conc. of Sulfuric Acid Aerosol by Spectroph., Coulometry and Flame Photo.", Anal. Chem. vol. 41, No. 6, May 1969, pp. 707–713.
Kerrigan et al., "Collection of Sulphuric Acid Mist in the Presence of Higher SO₂ Background", Anal. Chem., vol. 32, No. 9, Aug. 1960, pp. 1168–1171.

Primary Examiner—Ronald Serwin
Attorney, Agent, or Firm—Dowell & Dowell

[57] ABSTRACT

A method and apparatus for determining the level of sufuric acid in atmospheric air which also contains other interferrants, including a sampling cycle to collect sulfuric acid on the walls of a collection chamber tube which is cooled, while at the same time eliminating interfering sulfur dioxide and ammonia by treating them with a dilute flow of hydrochloric acid through the collection chamber, and further including an analysis cycle during which the walls of the collection chamber tube are heated so as to revolatilize the sulfuric acid and entrain it in a clean air stream which then passes to the burner block of a flame photometric detector, the clean air stream being saturated with water vapor to make the revaporization of sulfuric acid more rapid and complete. The apparatus includes a timing clock which operates valves to select the cooling and heating of the collection tube, and to initiate the timely introduction of sample ambient air streams, air carrying the hydrochloric acid, and the saturated air stream, as appropriate for the various different cycles of the system. The apparatus further includes a source of sulfuric acid entrained in a clean air stream which is used to check proper operation of the system in a mode of operation which is in the nature of a calibrating mode.

12 Claims, 6 Drawing Figures

FIG. 2.
| VALVE # | 49 | 50 | 51 | 52 | 53 | 54 | 55 | 56 | 57 | 58 | 59 | 60 |
|---|---|---|---|---|---|---|---|---|---|---|---|---|
| MEASUREMENT MODE — SAMPLING CYCLE | O | O | X | O | X | O | X | O | X | W | O | X |
| MEASUREMENT MODE — ANALYSIS CYCLE | X | X | O | X | X | X | X/O | O/X | O/X | W/A | X | X |
| OPERABILITY CHECK MODE — SAMPLING CYCLE | X | X | X | X | O | O | X | O | X | W | O | O |
| OPERABILITY CHECK MODE — ANALYSIS CYCLE | X | X | O | X | X | X | O | O/X | O/X | W/A | X | X |
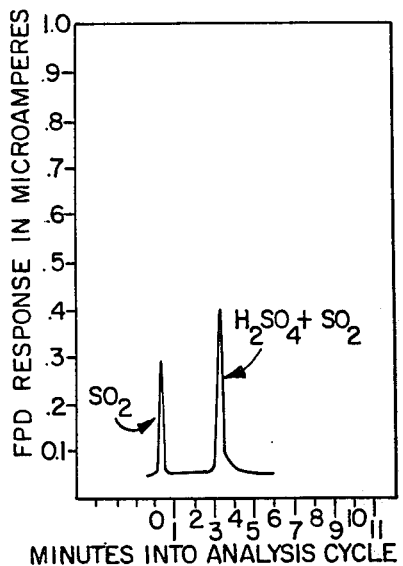
FIG. 3.
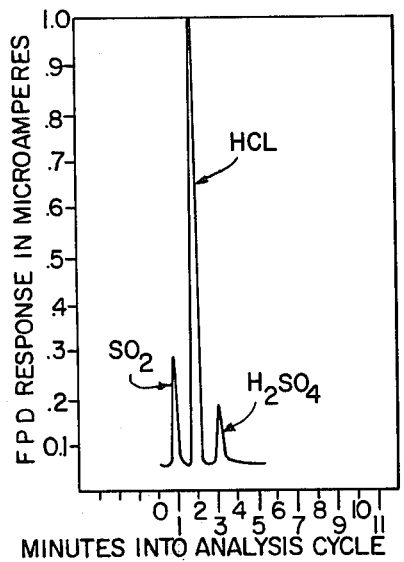
FIG. 4.
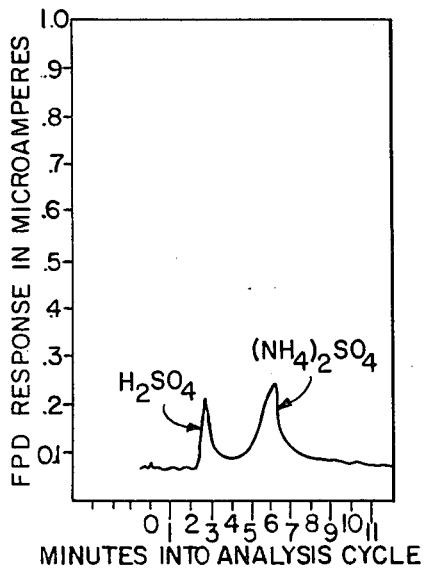
FIG. 5.
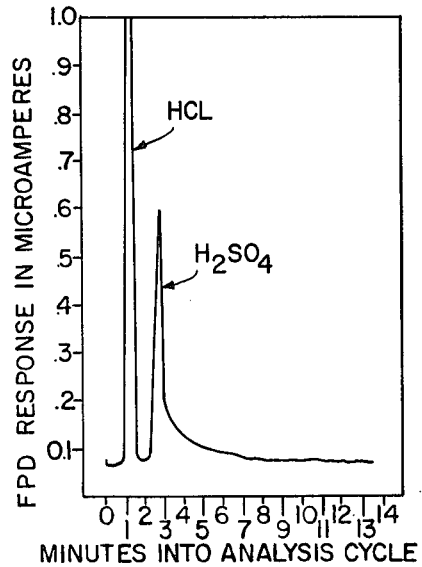
FIG. 6.

METHOD AND APPARATUS FOR ANALYSIS OF TOTAL ATMOSPHERIC SULFURIC ACID CONTENT

BACKGROUND AND PRIOR ART

The measurement of total concentration of sulfuric acid appearing in the atmosphere as an aerosol would be relatively easy if the sulfuric acid appeared by itself, since there are a number of ways of measuring low concentrations of sulfur in a sample stream. For instance, the flame photometric detector (FPD) is an instrument which is very sensitive when performing this type of measurement. However, as a practical matter when measuring atmospheric content of sulfuric acid the problem is made much more difficult by the presence of interferants in the sample stream, often appearing as sulfur dioxide and ammonium sulfates, etc. Since a flame photometric detector measures the total sulfur content in a sample stream, the presence of other compounds of sulfur provides incorrect readings. It would be a solution to the measurement problem if there existed an instrument sensitive only to sulfuric acid, and not to these other species as well, but no such instrument is known at the present time. The problem is further complicated by the fact that sulfuric acid in aerosol suspension is relatively unstable, and tends to react with other entrained species. This fact makes it highly desirable to actually analyze the sample air stream at the site, and immediately after it is taken, rather than attempting to collect a sample for later laboratory analysis.

This approach necessitates the provision of a method and apparatus capable of performing sophisticated sample handling steps for the purpose of isolating the sulfuric acid from interfering species so that it can be promptly transferred to the flame photometric detector for analysis at the sampling site. The present invention seeks to eliminate certain interfering species, while at the same time collecting the sulfuric acid droplets on the walls of a collection chamber, the interfering species being flushed through the chamber, and the apparatus subsequently revaporizing the sulfuric acid and delivering it to the flame photometric detector.

There are several prior art methods for determining sulfuric acid content in ambient air. For instance, one method includes exposing filters to large quantities of air for a protracted period of time to collect sulfuric acid which can then be analyzed when taken from the filter. One method and apparatus of this general type is discussed in an article entitled "Collection of Sulfuric Acid Mist In the Presence of a Higher Sulfur Dioxide Background", by James V. Kerrigan and Karl Snajberg and Edwin S. Anderson, the article appearing in Analytical Chemistry, volume 32, No. 9, August 1960 beginning at page 1168.

Another prior art method and apparatus is discussed in an article entitled "Determination of Atmospheric Concentrations of Sulfuric Acid Aerosol by Spectrophotometry, Coulometry and Flame Photometry" by Scaringelli and Rehme, appearing in Analytical Chemistry, volume 41, No. 6, May 1969 beginning at page 707. This article recognizes that there are interferants such as sulfur dioxide and sulfates of ammonia which are present, but the article seeks to solve the problem by chemically changing the sulfuric acid into other sulfur compounds which are then measured by the use of one of the well-known detection approaches such as spectrophotometry, coulometry or flame photometry. Therefore, the method and apparatus according to this article does not perform sequential steps designed to eliminate these interferants and then directly measure the level of sulfuric acid as is done in the present disclosure.

U.S. Pat. No. 3,948,602 to Solomon teaches the method of monitoring in air the level of chloromethyl ether which includes the use of a tube for collecting certain compounds, the tube then being heated to volatilize the compounds so that they can be transported in a carrier gas to a hydrogen flame detector. This apparatus has two cycles including a sampling cycle and an analysis cycle. This patent and U.S. Pat. No. 3,550,429 both use timers to determine the duration of cycles in the measuring process.

THE INVENTION

This invention teaches a method and apparatus for determining the level of sulfuric acid in atmospheric air which also contains other interferants such as sulfur dioxide and ammonia. Since there is no known apparatus which is sensitive only to the measurement of sulfuric acid content, it is necessary to remove the interferants before making a measurement of the remaining sulfuric acid level. The present invention teaches two separate steps including a sampling cycle designed to collect sulfuric acid on the walls of a collection chamber tube which is cooled, while at the same time eliminating interfering sulfur dioxide and ammonia by treating them with a dilute flow of hydrochloric acid through the collection chamber. The duration of the sampling cycle is made long enough to collect a significant quantity of sulfuric acid on the walls of the collection chamber, and therefore is selected on the basis of the expected concentration of sulfuric acid in the sample air stream introduced into the tube. The second step is an analysis cycle during which the walls of the collection chamber tube are heated so as to revolatilize the sulfuric acid and entrain it in a clean air stream which then passes to the burner block of a flame photometric detector. In order to provide virtually complete recovery of the sulfuric acid from the walls of the collection chamber when it is heated, this invention teaches the idea of using clean air which is saturated with water vapor to make the revaporization of sulfuric acid more rapid and complete. The present apparatus includes a timing clock which operates the necessary valves alternatively to select the cooling and heating of the collection tube, and to initiate the timely introduction of sample ambient air streams, air carrying the hydrochloric acid, and the saturated air stream, as appropriate for the various different cycles of the system. In order to determine that the system is operating properly, a source of sulfuric acid entrained in a clean air stream is provided which can be used to check proper operation of the system in a mode of operation which is in the nature of a calibrating mode used to analyze quantitatively an actual sample of ambient air.

It is a principle object of this invention to provide an improved method and apparatus for removing interfering species from an ambient air stream so that detectors sensitive to the presence of sulfur in the stream can be used to measure the remaining sulfuric acid entrained therein. The sulfuric acid appears mostly in the form of droplets suspended as an aerosol, although some sulfuric acid may exist in non-droplet molecular form. Since the sulfuric acid is highly active, it becomes necessary to measure its concentration virtually immediately after the sample is taken, as distinguished from returning a sample to the laboratory for later chemical analysis.

It is therefore a major object of this invention to provide a method and apparatus usable in the field to make immediate quantitative measurements of the concentration of sulfuric acid in the sample. The sample air stream is mixed with a dilute entrainment of hydrochloric acid in a clean carrier air stream, and the hydrochloric acid then removes ambient ammonia by changing it to particulate ammonium chloride and ammonium perchloride so that the ammonia does not react with the sulfuric acid to form ammonium sulfates, which of course would reduce the level of sulfuric acid in the sample. The hydrochloric acid also reacts with ambient sulfur dioxide to form particulate thionyl chloride, and these particulates then pass through the collection chamber and are exhausted outside the apparatus. The sulfuric acid is first vaporized in a heated transport tube and is then collected on the walls of a cooled collection chamber during the sampling cycle of the system.

Another major object of the invention is to provide improved ways for removing the collected sulfuric acid from the walls of the sampling chamber after the interferants have been flushed from the chamber by a stream of clean air. The system teaches the use of an air stream passing through the collection chamber whose walls have been heated to again volatilize the sulfuric acid. However, the invention further teaches that this stream of clean air must be humidified almost to saturation, or else the removal of the sulfuric acid from the chamber walls is much less complete and much slower, so that the walls of the chamber tend to continuously build up sulfuric acid which is not revaporized, whereby during successive operations of the system the measurements suffer from a cumulative error as a result of "memory effect" caused by the accumulating sulfuric acid. It is also believed that the collection chamber tube tends to become electrostatically charged on its surface and that these charges tend to retain the sulfuric acid against the wall of the tube. By introducing very humid air, the charges become neutralized by leakage between charged zones, whereby the sulfuric acid is more easily vaporized into the humidified air stream. The best materials for the transport tube and for the collection chamber have been found to be PTFE teflon or silanized glass, both of which are non-wetting materials.

Another major object of the invention is to provide a method and apparatus which are capable of reproducible results when measuring concentrations of sulfuric acid in gas streams. This reproducibility requires complete elimination of residual acid from the walls of the collection chamber during each analysis cycle so that subsequent sampling and analysis cycles of operation will not exhibit errors due to "memory effects".

Another object of the invention is to provide in the apparatus a built-in "calibrating" device, the word calibrating being somewhat inaccurate since the calibrating source of sulfuric acid in air is not really a precision source. However, the source used provides a substantially uniform flow of sulfuric acid entrained in air, and this is adequate for checking out the analyzing apparatus to verify its proper operation.

Another object of the invention is to provide means for quickly reheating the walls of the collection chamber during the analysis cycle of the system so as to achieve revaporization of the sulfuric acid and thereby permit complete operation of the system in a short period of time. The present improved reheating system together with humidification of the clean air stream reduces the elution and analysis cycle duration to about three to six minutes. In the sampling cycle of the system, the duration of the cycle depends upon the concentration of the sulfuric acid in the atmosphere. At a concentration of 5 micrograms per cubic meter, the sampling time needed is about three minutes, whereas for a concentration of 0.05 micrograms per cubic meter the sampling time must be about 90 minutes. The apparatus can analyze concentrations as low as about 0.01 micrograms per cubic meter. The apparatus is therefore provided with a timer having several different selectible time durations for the sampling cycle of its operation.

Still another object of the invention is to provide apparatus in which the sample transport tube and the collection chamber are made small in diameter, about 3/16 inch, so that the sample stream flows through the tube at a relatively high rate, whereby there is little tendency for particulate matter to fall out and collect within the tube. The sulfuric acid which enters the transport tube is first heated to about 400 degrees which vaporizes it so that it no longer appears as aerosol droplets. The sulfuric acid vapor is then condensed in the cooled collection chamber, but particulates pass on through and go out the exhaust at the other end of the transport tube. The heated transport portion of the tube is about two feet long, and the cooled collection chamber portion of the tube is about three feet long.

This invention is described in terms of an embodiment which is generally used at moderate ambient air temperatures, but this type of apparatus can also be used to sample at higher and lower sample stream temperatures, ranging between about minus 10 degrees C. and about a 1000 degrees C. The lower temperatures are of course still within ambient ranges, but the higher temperatures represent practical uses of the instrument to measure the amount of sulfuric acid in scrubbed stack gases wherein a typical temperature might be 260 degrees C. The stack gas without a scrubber typically runs considerably higher in temperature, of the order of 1000 degrees C. Internal cumbustion engine exhaust gases might run still higher. At these elevated temperatures, however, the sulfuric acid would already be vaporized, rather than in droplet form, and therefore it would only be necessary to lower the temperature of the sampling stream below the dew point in order to condense the sulfuric acid on the walls of the collection chamber.

A further object of the invention has been to provide an apparatus in which a readout of the concentration of sulfuric acid is provided in the form of a chromatogram showing peaks for the measured gas concentrations versus operating time in the cycle. The present invention has virtually eliminated the appearance of certain interfering species such as ambient sulfur dioxide, or species resulting from reactions between ambient ammonia and the sulfuric acid, which produce ammonium sulfates.

Other objects and advantages of the invention will become apparent during the following description of the drawings.

THE DRAWINGS

FIG. 2 is a diagram showing the positions of the valves in FIG. 1 during different cycles and modes of operation of the apparatus;

FIGS. 3 and 4 are related diagrams showing chromatograms for the system before and after introduction of hydrochloric acid vapor and showing the elimination of sulphur dioxide by its addition; and FIGS. 5 and 6 are related chromatograms showing the elimination of ammonia from the system by the addition of hydrochloric acid vapor.

PREFERRED EMBODIMENT

Figure 1:
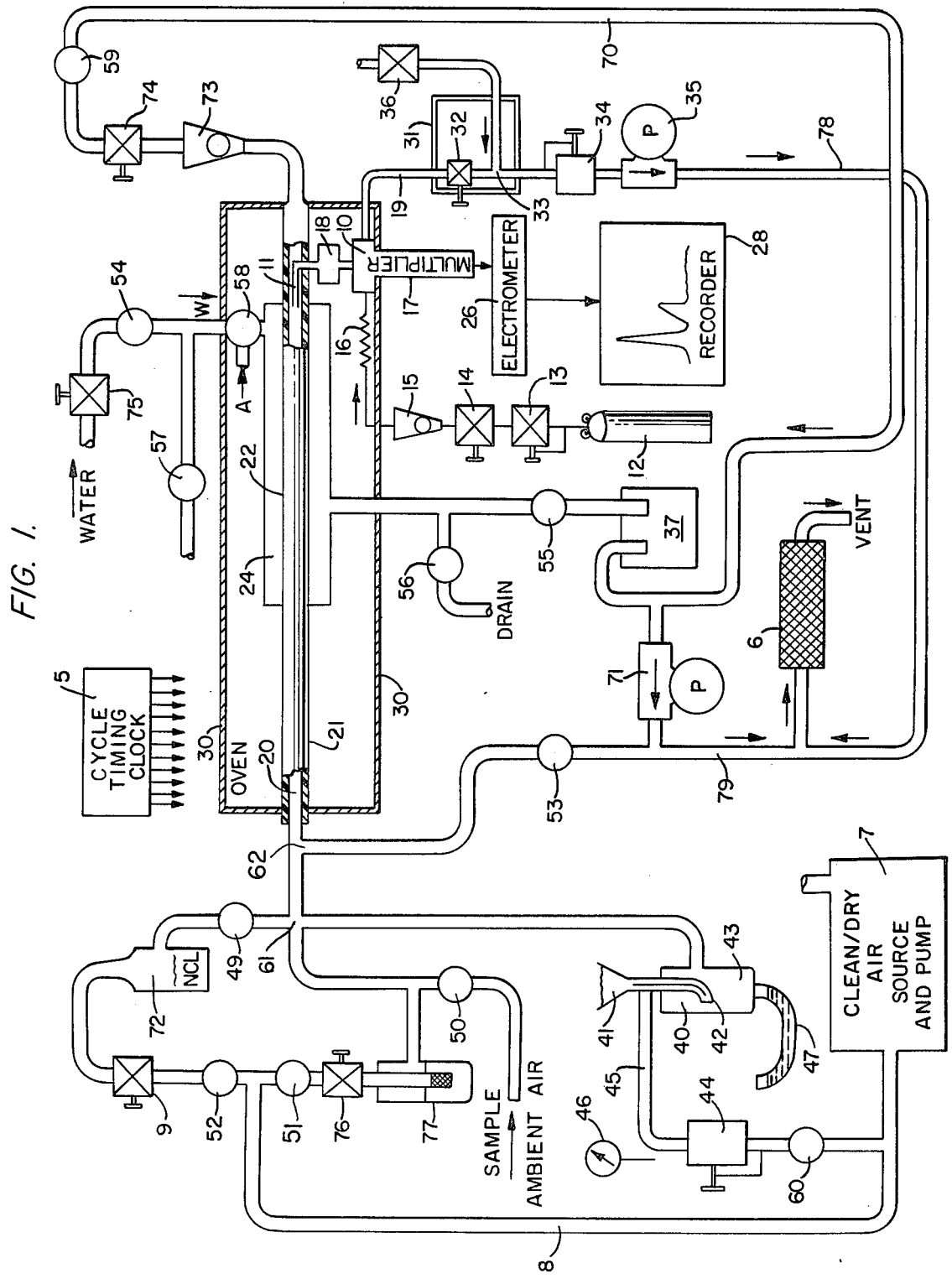
FIG. 1 is a diagram showing apparatus according to the present invention for measuring the content of sulfuric acid in the presence of other atmospheric species.

The apparatus according to the present invention basically includes a flame photometric detector 10 for detecting and measuring the amount of sulfur in a gas which is passed through a teflon transport tube 20, the flame detector with drawing the gas from within the teflon tube 20 via a small tube 11. The teflon tube 20 extends through an oven 30 which in the illustrative example is heated to about 400 degrees F. About two feet of the teflon tube 20 is continuously heated in the zone 21, and a three foot length of the tube 20 comprises a collection chamber 22 which is located inside of a surrounding jacket 24 which can be selectively heated or cooled in a manner to be hereinafter discussed. Thus, ambient air samples entering the transport tube 20 at the left proceed rightwardly and will first be heated in the hot transport zone of tube 21, and then chilled in the collection chamber 22 of the tube. If the coolant within the jacket 24 is subsequently drained and the chamber 22 of the tube is allowed to heat, condensate on the walls of the collection tube 22 will again be vaporized, and can be picked up by the smaller tube 11 and conducted to the FPD burner block located inside of the device 10. These are the basic components of apparatus serving to provide a measurement of the concentration of sulfuric acid in the sample entering the tube 20 from the left end.

The apparatus operates with two consecutive timed cycles including a sampling cycle during which samples are condensed on the inside of the collection chamber 22 of the tube, followed by a subsequent analysis cycle during which the samples collected in the chamber 22 are again vaporized and carried by the tube 11 into the FPD block 10. The change-over from one cycle to the next is accomplished by a number of valves located throughout the apparatus, the valves being operated by a suitable electrical timer 5 which repeats according to a sequence which is shown in FIG. 2 of the drawings.

The apparatus also functions in two different modes, the normal functioning being according to a measurement mode which includes two of said cycles, but there being also an operability checking mode in which the performance of the apparatus is checked out by introducing a sample gas stream of known sulfuric acid content which the system also processes using said two sequential cycles. These two modes of operation are also included in the table of FIG. 2 showing valve positions.

For purposes of the present discussion, it will be first assumed that the apparatus is operating in the measurement mode, which is its normal functional mode during actual use. At the beginning of the first cycle of operation, which is the sampling cycle, the timing clock 5 opens the valve 50 so as to induct sample ambient air from the surrounding atmosphere. This air is inducted through the valve 50, and passes through the cross connector 61 and through the tee 62 into the left end of the tube 20 where it is heated as it passes along through the continuously heated transport tube 21. The valve 59 beyond the far end of the collection chamber tube 22 is also open and is connected by a duct 70 which is coupled into a pump 71. The pump continuously sucks air through the tube 20, the valve 59 and the duct 70, and discharges it through an activated charcoal bed 6 whereupon the air is vented to the atmosphere. In addition, clean dry air is pumped from a source 7 through a duct 8 and through the open valves 52 and 49 to a flow regulator 9 which delivers a continuous flow at a regulated rate of about 100 c.c./minute to a source of hydrochloric acid, comprising a bottle 72 wherein the air is passed over a dilute solution of hydrochloric acid so that the air entrains a low level of the vapor and passes it through the cross connector 61 and through the tee 62 into the transport tube 20 to mix with the ambient air sample entering through the valve 50. As discussed above, the presence of the hydrochloric acid has the effect of removing from the transport tube 20 other sulfur compounds, in particular sulfur dioxide which forms particulate thionyl chloride, and also has the effect of removing ammonia from the tube 20 in the form of particulate ammonium chloride, these particulates passing outwardly through the exhaust valve 59 as the air flows through the transport tube 20. A flow meter 73 and a flow regulator 74 regulate the flow through the tube 20 so that the rate is uniform at about 200 c.c./minute. It is necessary that the rate be maintained uniform since the sulfuric acid collected on the walls of the chilled tube portion 22 will then be a function of time as determined by the timing clock 5. As stated above, the mixture of ambient air plus the clean air containing hydrochloric acid vapor has prior to cooling been heated in the transport tube 21.

Since this is a sampling cycle whose purpose is to accumulate sulfuric acid on the inner walls of the collection chamber tube 22, this tube must be cooled so that condensation will occur. Cooling is accomplished by passing water, for instance at about 55 degrees F. through a pressure regulator 75 and through the valves 54 and 58 into the jacket 24 which surrounds the collection chamber 22 of the teflon tube. The valves 55 and 57 are closed, but the valve 56 is open to discharge the cooling water after it passes through the jacket 24. The valves remain in these positions during the sampling cycle so that the jacket 24 is continuously cooled to a temperature below the dew point of the sulfuric acid entrained in the ambient air. The pump 71 continuously draws this mixture through the tube 20 for a period of time determined by the sampling cycle interval selected by the timing clock 5. The valves 53 and 60 are closed during each sampling cycle of the measurement mode of operation as shown in FIG. 2.

The timed interval of the sampling cycle is selected from among several preset timing intervals so that the duration of the sampling cycle can be increased by the operator when ambient air is being sampled which has a relatively low concentration of sulfuric acid to be measured, and conversely decreased when measuring a relatively high concentration of sulfuric acid in the ambient air being sampled.

During the analysis mode, the valves are reset in different positions by the timing clock. In this analysis mode, the valves 60 and 53 still remain closed, but in addition the valve 50 is closed so that no more ambient air is inducted, and the valves 49 and 52 are closed so that no more hydrochloric acid vapor is introduced into the airstream entering the tube 20 through the cross connector 61 and the tee 62. However, the valve 51 is opened so that clean dry air from the air source 7 passes through the duct 8, through the valve 51 and enters the transport tube 20 by passing through a flow regulator 76 and through a humidifier 77 which has water contained in the bottom thereof, the air entering from the regulator 76, bubbling through the water and then passing outwardly from the humidifier through the cross connector 61 and the tee 62 into the transport tube 20. The valve 53 remains closed.

Moreover, at the beginning of the analysis mode, the valve 54 is closed so that no further cooling water enters the jacket 24. The valve 57 is opened at the beginning of the analysis mode, and the valve 56 is also left open for a short while so that the water drains out of the jacket 24. Shortly after the beginning of the analysis cycle when the jacket has emptied, the valves 57 and 56 are closed, and the valve 58 is reversed so as to allow hot air from within the oven to enter the jacket 24 through the valve 58. At the same time, the valve 55 is opened so that the pump 71 draws heated air from inside the jacket 24 through the valve 55, through a water trap 37 and the pump 71, and discharges it through the charcoal bed 6 so that it is vented to the atmosphere. Thus, the collection tube 22 begins to rapidly heat toward the temperature of the oven, and this is done for the purpose of revaporizing sulfuric acid deoplets from the walls of the collection tube 22 so that they can be collected by the flame detector 10 through the tube 11. The valve 59 is also closed during the analysis cycle so that all air passing from the tube portion 22 must depart through the flame detector 10, none of it being exhausted directly to the atmosphere. The air entering the transport tube 20 is clean air from the source 7 humidified by the humidifier 77 so that it is virtually saturated with water vapor. This is the only air entering the transport tube 20 during the analysis cycle.

Referring now to the FPD flame detector in greater detail the burner block 10 contains a gas flame which is fed from a bottle 12 containing hydrogen gas passing through a pressure regulator 13 and a flow regulator 14 to a flow meter 15, the gas then being preheated by a heat exchanger 16 located inside of the oven 30 and passing into the burner (not shown) within the burner block 10. A photomultiplier tube 17 is located opposite the burner and is connected with external electronics which will be discussed hereinafter for providing an indication of the concentration of sulfuric acid measured by the FPD. The transport air being introduced into the tube 20 is collected in the smaller tube 11 and passes downwardly through a pressure surge eliminator 18 which serves the purpose of smoothing out any sudden changes in pressure or flow rate which may occur, especially at times when the valves are being reversed for the purposes of changing between sampling and analysis cycles of operation. Without the surge eliminator 18, sudden changes of pressure tend to create a flow into the burner block which extinguishes the flame. After the air passing through the surge eliminator 18 passes over the flame, it is withdrawn downwardly into the duct 19 and passes into a temperature controlled enclosure 31 which contains a flow regulator 32. The regulator 32 delivers a flow of gas downwardly past tee 33 and into a vacuum regulator 34, the vacuum being supplied by the vacuum pump 35. At the tee 33, air is entered from the atmosphere through a fixed impedance orifice 36, and this atmospheric air is supplied to the tee 33 for the purpose of lowering the humidity of the exhaust flowing toward the vacuum regulator 34 in order to prevent condensation thereof. The gas passing through the vacuum pump 35 is then carried through the duct 78 and delivered into the charcoal bed 6, beyond which it is vented to the atmosphere.

The FPD burner block functions to measure the total amount of sulfur in the gas samples. At the end of the sampling cycle and the beginning of an analysis cycle, the sulfuric acid droplets are collected on the internal surface of the collection tube 22 which at that time is still chilled by cooling water passing through the jacket 24. When the apparatus changes from the sampling cycle to the analysis cycle, one of the changes is to remove the water from the jacket 24 and replace it with heated air from the oven as described above. Thereupon, the portion 22a of the transport tube 20 starts heating toward the oven temperature, and the heating of the tube revaporizes the sulfuric acid so that it will be entrained in the humidified clean air being flushed through the transport tube 20 from the humidifier 77. The sulfuric acid which is being revaporized and entrained in the air passing through the tube 20 is all collected by the smaller tube 11 and passes through the flame detector so that the photomultiplier tube 17 delivers information to the electronics which then displays an indication of the sulfur content. The output of the photomultiplier 17 is delivered to an electrometer 26 which delivers output voltage signals representative of the amplitude of the species being detected in the FPD 10, and a recorder plots these amplitudes vertically against a horizontal time axis, as shown in FIGS. 3, 4, 5 and 6.

FIG. 3 shows a chromatogram plot against time into the FPD analysis cycle of the intensity of the signal when a gas stream containing sulfuric acid in a concentration of about 10.8 μg/M3 and sulfur dioxide gas at about 90 p.p.b. has been introduced into the sample air inlet of the apparatus, but no hydrochloric acid was introduced therewith. FIG. 4 shows a plot of the same mixture but with hydrochloric acid vapor also introduced therewith. Note that in FIG. 4, the amplitude of the sulfuric acid response is smaller than in FIG. 3. This is attributable to the fact that the sulfuric acid response in FIG. 3 is not a response only to the sulfuric acid concentration, but is a response to the sulfuric acid plus such sulfur dioxide as has been absorbed by and adsorbed onto the sulfuric acid droplets. Therefore the addition of hydrochloric acid has reduced the trace response of the recorder to read the level of sulfuric acid per se to thereby provide a correct indication thereof without sulfur dioxide added to that trace.

FIG. 5 shows a chromatogram plot against time into the FPD analysis cycle of the intensity of the signal when a gas stream containing sulfuric acid in a concentration of about 10.8 μg/M3 and ammonia gas at about 52 p.p.b. has been introduced into the sample air inlet of the apparatus, but no hydrochloric acid vapor was introduced therewith. FIG. 6 shows a plot of the same mixture but with hydrochloric acid vapor also introduced therewith. Note that in FIG. 6 the sulfuric acid trace is higher and more sharply defined, and that the ammonium sulfate trace has disappeared entirely. The greater amplitude of the sulfuric acid trace in FIG. 6 is attributable to the elimination of the ammonia as ammonium chloride, whereby the ammonia is not degrading the quantity of sulfuric acid present by converting it into sulfates of ammonia.

It is highly desirable to provide another mode of operation by which the performance of the apparatus can be checked out. For this purpose, a nebulizer is provided which can be selectively connected to deliver a standardized flow of sulfuric acid aerosol into the transport tube 20. This is done during the calibration checking mode which operates in two sequential cycles as follows:

In the illustrated embodiment, the nebulizer takes the form of a Baird-Atomic atomizer 40 which holds a quantity of sulfuric acid in a feed device 41 leading to a nozzle 42 within a bottle 43. The atomizer 42 is operated by clean dry air which is forced through a pressure regulator 44 into a duct 45, the pressure being indicated on a gauge 46. During the sampling cycle of the calibration checking mode, the valve 60 is open, and clean air is forced through the nozzle so as to atomize sulfuric acid into the bottle 43. Most of the atomized acid runs down the sides of the bottle and leaves by a manometer 47 at the bottom thereof, but a substantially constant amount of sulfuric acid aerosol is entrained in the air and passes into the sample duct and travels through the cross connector 61 and through the tee 62 into the transport tube 20. The Baird-Atomic atomizer 40 will not operate with a very low flow of air through the atomizer 42, and therefore some of the flow must be diverted from the tube 20 by opening the valve 53 and allowing the excess flow to pass downwardly through the duct 79 into the charcoal bed 6 to be vented therefrom. With the regulator 44 set correctly, the flow through the atomizer is about 20 liters/minute, but the tube 20 can handle only about 10 liters/minute. The latter flow passes entirely outwardly through the flow meter 73 and the flow regulator 74 and through the valve 59 which is open during this sampling cycle, and is discharged through the charcoal bed 6 into the atmosphere. The remaining 10 liter/minute flow passes through the valve 53 and is vented to the atmosphere.

In the calibration sampling mode, as distinguished from the measurement sampling mode, the valve 50 is closed to keep out ambient air and the valves 51, 52 and 49 are also closed. However, water must be again introduced to cool the jacket 24, and therefore the valve 54 is open, the valve 58 is set to admit water into the jacket 24, the valves 55 and 57 are closed, and the valve 56 is opened to discharge the water after it has flushed through the jacket 24. Thus, the enriched air containing sulfuric acid from the Baird-Atomic atomizer 40 is heated in the transport tube 21 and then is condensed and collected in the collector tube 22 which is within the cooling jacket 24. The timer 5 continues the sampling cycle of operation until a sufficient time has passed in order to deposit a significant condensate of sulfuric acid upon the transport collection chamber 22, and at this point in time the system reverses to the analysis cycle.

In the analysis cycle of the calibration checking mode, the valve 50 remains closed, but the valve 51 is opened to permit clean air to pass through the regulator 76 and the humidifier 77 into the transport tube 21 via the tee 62. The valves 53, 52 and 49 are closed, and the valve 54 is also closed so as to prevent any more cooling water from entering the jacket 24. The valves 56 and 57 are momentarily opened, and the water therefore drains out through the valve 56 and is discharged so that the jacket 24 is emptied of water. The valve 58 then reverses so as to admit heated air from the oven into the jacket 24, and the valves 56 and 57 are closed. The timer opens the valve 55, and the pump 71 pulls heated air through the valve 58 to heat the jacket 24, the air being pulled downwardly through the valve 55, through a water separation chamber 37, and then outwardly through the pump 71 and through the charcoal bed 6 to be discharged into the atmosphere. This flow of heated air through the jacket 24 results in rapid heating of the collector portion 22 of the transport tube 20, thereby revaporizing the sulfuric acid from the walls of the collector tube 22, and delivering it all into the burner block 10 through the smaller tube 11, the valve 29 being closed during the analysis cycle. The FPD then analyzes the quantity of sulfuric acid which was revaporized from the collector portion 22 of the transport tube 20, and the electronic system displays a chromatogram showing the total quantity of sulfuric acid which was deposited on the transport collector tube 22 during the timed interval of the sampling cycle of the apparatus. From this readout, a check of the operability of the apparatus can be made knowing that a standardized quantity of sulfuric acid was introduced into the transport tube 21, and this readout provides a check of the calibration of the apparatus.

This invention is not to be limited to the exact embodiment shown in the drawings, for obviously changes may be made within the scope of the following claims.

I claim:

1. The method of collecting atmospheric sulfuric acid contained in an ambient air stream containing interfering sulfur dioxide and ammonia species, and analyzing sulfuric acid content after eliminating the interfering species, comprising the steps of:
    (a) mixing the air stream with a clean air stream entraining dilute hydrochloric acid;
    (b) heating the mixed air streams to a temperature above the vaporization point of sulfuric acid;
    (c) passing the air streams over a surface cooled to a temperature below the dew point of sulfuric acid to condense the sulfuric acid;
    (d) subsequently heating said surface to a temperature above the vaporization point of sulfuric acid while flushing it with a clean carrier gas substantially saturated with water vapor to entrain the sulfuric acid; and
    (e) analyzing the carrier gas and entrained sulfuric acid while integrating the total quantity of sulfur contained therein.

2. The method as claimed in claim 1, wherein the duration of the step of passing the air streams over the cooled surface is timed according to an interval designed to collect sufficient sulfuric acid on said surface to permit subsequent analyzing thereof, the duration being selected inversely with respect to the expected concentration of sulfuric acid in the ambient air stream.

3. The method as claimed in claim 2, wherein the duration of the step of flushing the surface with the heated carrier gas is proportional to the time required to heat the surface from said temperature below the dew point to said temperature above the vaporization point of sulfuric acid.

4. The method as claimed in claim 1, wherein the step of passing the air streams over the cooled surface includes impinging the air stream on the surface at a velocity sufficiently high to flush particulates from the surface.

5. The method as claimed in claim 1, wherein the step of analyzing the carrier gas and entrained sulfuric acid includes flame photometric detection of the total sulfur contained therein.

6. Apparatus for collecting and analyzing the total sulfuric acid content in an ambient air stream containing interfering sulfur dioxide and ammonia species while eliminating the interfering species during said collecting and prior to said analyzing, comprising:
(a) a transport chamber heated to a temperature above the vaporization temperature of sulfuric acid;
(b) a collection chamber coupled to said transport chamber and having selectively actuatable means for cooling the collection chamber to a temperature below the dew point of sulfuric acid and alternatively for heating the collection chamber to a temperature above said vaporization temperature;
(c) a source of dilute hydrochloric acid vapor entrained in a clean air stream;
(d) pump means for passing the hydrochloric acid vapor air stream and the ambient air stream through both chambers in intimate mutual contact;
(e) a source of clean carrier gas substantially saturated with water vapor;
(f) detector means connected to said chambers and operative to detect the quantity of sulfur in a stream; and
(g) cyclically operating time clock and valve means coupled with the chambers and sources and detector means and operative during a sampling cycle to actuate said collection chamber cooling means and said valve means to pass said hydrochloric acid and ambient air streams through the chambers while condensing and collecting sulfuric acid on the collection chamber, and operative during a subsequent analysis cycle to actuate said collection chamber heating means and said valve means to flush the said saturated carrier gas through the chambers and through said detector means to entrain revaporized sulfuric acid in the carrier gas and carry it through the detector means.

7. The apparatus as claimed in claim 6 wherein said transport and collection chambers comprise series connected tubes having interior surfaces of non-wetting plastic material the diameters of the tubes being very small as compared with their lengths to maintain the velocity of flow high, whereby to remove particulates therefrom.

8. The apparatus as claimed in claim 6, wherein the collection chamber is connectable by said valve means selectively between a vent to the atmosphere which is operative during each sampling cycle, and said detector means into which it discharges during each analysis cycle.

9. The apparatus as claimed in claim 6, wherein said transport and collection chambers comprise a teflon tube passing through an oven, the transport chamber portion of the tube being heated thereby, and the collection chamber portion of the tube being surrounded by a jacket; and the apparatus having means controlled by said valve means for selectively passing heating and cooling media through said jacket.

10. The apparatus as claimed in claim 6, wherein said pump means includes means for regulating the rate of flow of said air streams through the chambers.

11. The apparatus as claimed in claim 6, wherein said valve means is operative to shut off the flow of carrier gas during the sampling cycle, and to shut off the flow of said air streams during the analysis cycle.

12. The apparatus as claimed in claim 6, wherein said time clock and valve means are further capable of performing selectively a two-cycle measuring mode as claimed in claim 6, and a two-cycle operability checking mode, the apparatus further including a source of clean gas; a source of sulfuric acid; means operative to entrain a standardized concentration of the sulfuric acid in a stream of the clean air; and said time clock and valve means being operative during said operability checking mode to substitute during a sampling cycle said clean air stream entraining said sulfuric acid instead of said hydrochloric acid and ambient air streams to condense a known quantity of sulfuric acid on the collection chamber, and being operative subsequently during an analysis cycle to pass said carrier gas through the collection chamber and entrain the sulfuric acid therefrom and carry it through the detector means.

* * * * *